United States Patent
Krumhar

(10) Patent No.: US 6,949,260 B2
(45) Date of Patent: Sep. 27, 2005

(54) METHOD FOR TREATMENT OF INFLAMMATION AND PAIN IN MAMMALS

(75) Inventor: Kim Carleton Krumhar, Carlsbad, CA (US)

(73) Assignee: Metagenics, Inc., San Clemente, CA (US)

( * ) Notice: Subject to any disclaimer, the term of this patent is extended or adjusted under 35 U.S.C. 154(b) by 0 days.

(21) Appl. No.: 10/378,572

(22) Filed: Mar. 3, 2003

(65) Prior Publication Data

US 2003/0185907 A1 Oct. 2, 2003

Related U.S. Application Data

(63) Continuation of application No. 09/519,527, filed on Mar. 6, 2000, now Pat. No. 6,534,086.

(51) Int. Cl.$^7$ .......................... A61K 33/42; A61K 35/78
(52) U.S. Cl. ........................ 424/601; 424/602; 424/725; 424/734; 424/757
(58) Field of Search ................................. 424/601, 602, 424/728, 734, 757, 760, 769, 725

(56) References Cited

U.S. PATENT DOCUMENTS

| | | | | |
|---|---|---|---|---|
| 5,804,594 A | | 9/1998 | Murad | |
| 5,885,597 A | * | 3/1999 | Botknecht et al. | 424/401 |
| 5,972,382 A | | 10/1999 | Majeed et al. | |
| 6,210,701 B1 | | 4/2001 | Darland et al. | |
| 6,344,220 B1 | * | 2/2002 | Rose et al. | 424/725 |
| 6,352,712 B1 | | 3/2002 | Lukaczer et al. | |
| 6,358,539 B1 | | 3/2002 | Murad | |
| 6,492,429 B1 | * | 12/2002 | Graus et al. | 514/688 |

FOREIGN PATENT DOCUMENTS

| | | |
|---|---|---|
| WO | WO 00/12085 | 3/2000 |
| WO | WO 02/07768 | 1/2002 |

OTHER PUBLICATIONS

Datasheet,"Inflavonoid Intensive Care™" Curcumin & Boswellia Complex, downloaded from internet on Mar. 28, 2002: http://www.doctorshealthsupply.com/metagenics/inflavonoid_intensive_care.htm, last edited Feb. 26, 2002 11:44 p.m., pp. 1–3.

Kiuchi, F., et al.; Inhibition ofProstaglandin and Leukotriene Biosynthesis by Gingerols and Diarylheptanoids; Chem Pharm Bull 1992; 40(2): 387–391.

Garrett, NE, et al.; Effect of capsaicin on substance P and nerve growth factor in adjuvant arthritic rats; Neuroscience Let 1997; 230(1):5–8.

Ammon, HP, et al.; Mechanism of antiinflammatory actions of curcumine and boswellic acids; J Ethnopharmacology 1993; 38(2–3): 113–119.

Safayhi H.; Boswellic Acids: Novel, Specific, Nonredox Inhibitors of 5–Lipoxygenase; J Pharmacol Exp Ther 1992; 261(3): 1143–1146.

Kulkami RR, et al.; Treatment of osteoarthritis with a herbomineral formulation: a double–blind, placebo–controlled, cross–over study; J. Ethnopharmacology 1991:33 (1–2): 91–95.

Srivastava KC, et al.; Ginger (Zingiber officinale) in Rheumatism and Musculosskeletal Disorders; Med Hypotheses 1992; 39(4): 342–348.

Guh JH, et al.; Antiplatelet Effect of Gingerol Isolated from Zingiber officinale; J Pharmacol 1995; 47(4):329–332.

Kaul TN, et al.; Antiviral Effects of Flavonoids on Human Viruses; J Med Virol 1985;15: 71–79.

Vrijsen R., et al.; Antiviral Activity of Flavones and Potentiation by Ascorbate; J Gen Virol 1988; 69:1749–51.

* cited by examiner

Primary Examiner—Herbert J. Lilling
(74) Attorney, Agent, or Firm—McDermott Will & Emery LLP

(57) ABSTRACT

A composition for treating inflammation and pain in mammals, particularly humans. Effective amounts of a boswellic acid, a curcuminoid, a gingerol, a capsaicinoid, a bioflavonoid, and a vitamin C source, in various combinations, all preferably from a botanical source, are blended to form a dose for oral administration. Administration of the dose provides relief from pain and inflammation of connective tissue. The dose may be administered as a tablet, a liquid, or a powder.

11 Claims, No Drawings

METHOD FOR TREATMENT OF INFLAMMATION AND PAIN IN MAMMALS

This application is a continuation of U.S. application Ser. No. 09/519,527, filed Mar. 6, 2000 now U.S. Pat. No. 6,534,086.

BACKGROUND

1. The Field of the Invention

This invention relates compositions and methods used to prevent and treat inflamation in mammals. More particularly, the present invention relates to compositions and methods for reducing inflamation and pain associated with acute inflammation of mammalian body parts, particularly joints, due to injury or due to arthritic conditions or other disease conditions.

2. The Background Art

Millions of people and animals suffer pain due to inflamation of connective tissue, including joints and other body parts. The suffering which is encountered ranges from mild soreness to debilitating pain which prevents any motion of the afflicted body part.

The term "connective tissue" loosely refers to the tissues which hold a body together. Connective tissue disease is the term used to generally describe a long list of afflications which involve connective tissue. Connective tissue is present in all organs, so the term connective tissue diseases describes a group of diseases which influence a wide range of different body systems.

Rheumatic diseases, which are one type of connective tissue disease, include a variety of different conditions. However, a common feature a rheumatic diseases is that they all involve joints and the surrounding tissues such as ligaments, tendons and muscles. Rheumatic diseases can involve other, seemingly unrelated organs as well, such as eyes, skin and glands. Rheumatic diseases are usually divided into those that primarily involve joints, known as arthritis, and those involving other tissues, generally referred to as connective tissue diseases. Arthritis is further subdivided into inflammatory and non-inflammatory arthritis.

One of the most common forms of connective tissue disease is osteoarthritis which is a non-inflammatory type of arthritis. Osteoarthritis is generally considered to be due to "wear and tear" of the joints leading to damage of the joint surfaces which results in pain on movement of the joint. There are many factors influencing development of osteoarthritis, including a family history of osteoarthritis and previous damage to the joint caused by injury or surgery. Osteoarthritis is very common in older age groups, but can afflict younger people and animals.

Symptoms in osteoarthritis tend to get worse with activity, so that the greatest pain is experienced at the end of the day. In contrast, the symptoms of inflammatory arthritis include the greatest pain occurring at the movement of a joint after a night's sleep of inactivity. In the case of osteoarthritis, there may be hard, bony swelling of the joints, and a gritty feeling (or even noise) when the joint is moved.

The term arthritis also refers to conditions where inflamation occurs in a joint. While some in the field use the term "arthritis" to strictly mean inflammation of the joints, the term is used more generally for almost all joint problems. So the term "inflammatory arthritis" generally means those diseases of joints where, for example, the immune system is causing inflammation in the joint. Among the more common types of inflammatory arthritis are rheumatoid arthritis, gout, psoriatic arthritis (associated with the skin condition psoriasis), reactive arthritis, viral or post-viral arthritis (occurring after an infection), and spondylarthritis which affects the spine as well as joints.

These different types of arthritis all have many features in common, so that it may be impossible to say exactly what type of arthritis a patient is afflicted with. This is especially true at the onset of arthritis, as the early symptoms are generally common to all types. As a rule, any type of arthritis can affect any joint, but some patterns of affected joints are typical of particular types of arthritis, as discussed below.

The characteristic symptoms of inflammatory arthritis are pain and swelling of one or more joints. The afflicted joints are often warmer than the other joints of the body. Stiffness of the joints when getting up in the morning, or after sitting still for a time, is very common and is sometimes the first symptom. These symptoms may begin after a minor illness such a sore throat or a cold, or may even be associated with a period of emotional stress such as a bereavement. Usually, however there is no identifiable cause associated with the commencement of inflammatory arthritis.

Moreover, there are many common minor pains which are not arthritis but are due to injury, strain or inflammation of tendons or ligaments and are referred to as "soft tissue rheumatism." Some of the more common soft tissue rheumatism conditions which afflict humans include tennis elbow, frozen shoulder, carpal tunnel syndrome, plantar fasciitis, and Achilles tendonitis.

Tennis elbow is due to inflammation of the tendons of the hand gripping muscles where these tendons are attached to the elbow. This results in pain at the elbow, worse on gripping with the hand, and the afflicted area is tender when pressed. It usually gets better by itself if the hand is rested, but the condition can recur. Conventional treatment includes injection of steroids at the tender spot. As is well appreciated, tennis elbow is not confined to tennis players.

Frozen shoulder is a stiffening of the ligaments around the shoulder joint which usually comes on after prolonged unaccustomed use of the arm, such as painting a ceiling. When afflicted with frozen shoulder, it is painful and difficult to move an arm in any direction. In this condition, it is important to start treatment quickly since delay will make the condition more difficult to treat. Past treatment has included a program of exercises to slowly increase the range of movement of the arm with a steroid injection into the shoulder to get it moving again.

Carpal tunnel syndrome involves a nerve which passes through the carpal tunnel on the front of the wrist into the human hand. When this tunnel becomes inflamed it can press on the nerve causing shooting pain into the thumb and first two fingers. The syndrome can arise due to many conditions such as thyroid disease, pregnancy and arthritis. Symptoms are often worse at night keeping the sufferer awake. Past treatments include steroid injections and rest. In some cases, surgery to open up the tunnel may be necessary.

Plantar fasciitis involves ligaments in the sole of the foot which can get inflamed leading to pain on the bottom of the heel while walking. Steroid injections and orthotic shoe devices have been used to treat the condition.

Achilles tendonitis involves the Achilles tendon located at the back of the human ankle and which becomes inflamed and painful when walking or especially painful to stand up on tip-toe. This condition is usually caused by shoes which rub at the back of the heel. Further information regarding these afflictions can be obtained from Arthritis Foundation (see http://www.arthritis.org and the links provided thereat as of the filing of this application).

All of these conditions and afflictions are the subject of continuing research looking for better treatments. For many arthritis sufferers, an improved treatment would include one which does not require the consumption of over-the-counter or prescription drugs. Moreover, many people suffer from afflictions attacking organs such as the skin and muscles and expressing symptoms via headaches and backaches, all of which would benefit from better treatments. For example, treatments utilizing botanical compositions can benefit many patients and provide advantages not otherwise available.

OBJECTS AND BRIEF SUMMARY OF THE INVENTION

In view of the above described state of the art, the present invention seeks to realize the following objects and advantages.

It is a primary object of the present invention to provide a composition used to treat mammals which reduces acute and chronic inflammation.

It is also an object of the present invention to provide a composition which is orally administered which reduces inflammation in mammals.

It is also an object of the present invention to provide a composition for use as a dietary supplement which, when ingested, is effective in treating the pain and discomfort of inflammatory ailments such as, but not limited to, rheumatoid arthritis, osteoarthritis, juvenile rheumatoid arthritis, soft tissue rheumatism, gout, low back pain, minor soft tissue injuries, minor burns and other skin injuries and afflictions, sprains, headache, backache, and general muscle soreness after exercise and exertion.

It is another object of the present invention to provide a composition for use as a dietary supplement which, when ingested on a regular basis, improves the use of joints which are afflicted with arthritis.

It is still another object of the present invention to provide a dietary supplement which reduces the swelling, pain and morning stiffness of arthritic joints and which increases range of motion, grip strength and general mobility in affected joints.

It is yet another object of the present invention to provide a dietary supplement composition which improves the general health, quality of life, and well being of those suffering from chronic inflammatory diseases, including rheumatism and arthritis.

It is a yet further object of the present invention to provide a safe and effective dietary supplement composition which can be used to reduce the dosage of, or replace conventional Non-Steroidal Anti-Inflammatory Drugs (NSAIDs), for the symptomatic treatment of pain, inflammation and swelling in mammals.

It is also an object of the present invention to provide a safe and effective composition for the treatment of pain, inflammation and swelling in individuals for whom NSAIDs are no longer desirable due to gastrotoxicity, gut intolerance or risk of renal damage.

It is a further object of the present invention to provide a composition which is formulated using rigorously and correctly identified, analyzed, and documented botanical ingredients from which active ingredients have been water extracted to prepare a concentrate, which is dried, and which results in the end composition standardized to contain minimum levels of certain indicator phytochemicals having the desired physiological attributes.

These and other objects and advantages of the invention will become more fully apparent from the description and claims which follow, or may be learned by the practice of the invention.

The present invention provides a composition for treating inflamation and pain in mammals, particularly humans. In one preferred composition, an effective amount of a boswellic acid, the boswellic acid being derived from a botanical source, and an effective amount of a curcuminoid, the curcuminoid being derived from a botanical source, are blended to form a dose for oral administration to the human or other mammal. Administration of the dose provides relief from pain and inflamation of connective tissue.

In one preferred dose of the composition, the effective amount of boswellic acid comprises from about 10 to about 1800 milligrams of *Boswellia* gum extract and more preferably about 100 to about 800 milligrams of *Boswellia* gum extract. Other preferred sources of boswellic acid include extracts of: *Boswellia serrata, Boswellia bhau-dajiana, Boswellia frereana, Boswellia papyrifera,* Sudanese *Boswellia sacra,* and *Boswellia carterii, Commiphora incisa, Commiphora myrrha, Commiphora abyssinica, Commiphora erthraea, Commiphora molmol,* and *Bursera microphylla.* The extract providing the boswellic acid preferably comprises in the range from about 20% to about 40% by weight of the dose.

In the preferred dose of the composition, the effective amount of curcuminoid comprises from about 50 milligrams to about 400 milligrams of curcuminoids and more preferably about 100 milligrams to about 300 milligrams of curcuminoids. Preferably, the curcuminoids are contained in a tumeric rhizome extract. The extract providing the curcuminoid preferably comprises in the range from about 5% to about 40%, and more preferably from about 10% to about 30%, by weight of the dose.

In another preferred embodiment of the invention, the formulation can also contain an effective amount of gingerol, the gingerol being derived from a botanical source. The gingerol is preferably obtained from ginger rhizome extract. The amount of gingerol in the composition is preferably about 1 to about 200 mg, more preferably about 1 to about 100 mg, and most preferably about 2 to about 50 mg.

The preferred doses of the present invention may also include an effective amount of capsaicin, an effective amount of an antioxidant, an effective amount of flavonoids (for example, quercetin or isoquercetin), and/or an effective amount of vitamin C. The extract providing the capsaicinoid preferably comprises in the range from about 1% to about 25%, and more preferably from about 1% to about 15%, by weight of dose. The extract providing the bioflavonoid preferably comprises in the range from about 1% to about 25%, and more preferably from about 1% to about 20%, and most preferably from about 2% to about 20%, by weight of the dose. The dose may be administered as a tablet, a liquid, or a powder.

In another preferred embodiment of the invention, the present invention further comprises effective amounts of certain minerals, such as calcium and phosphorus. In tablet form, the present invention can further comprise additives for imparting satisfactory compression characteristics to the formulation, including diluents, binders, and lubricants, and for giving additional desirable physical characteristics to the finished tablet, such as disintegrators, colors, flavors, and sweetening agents.

One method of treating a mammal in accordance with the present invention to reduce inflamation in connective tissues includes the steps of: extracting from a first botanical sample an amount of a boswellic acid, the first botanical sample being at least one selected from the group consisting of genus *Boswellia , Commiphora,* and *Bursera* or closely related woody plant species of the family *Burseraceae* to derive a Boswellic acid extract; extracting from a second botanical sample an amount of a curcuminoid, the second botanical sample being at least one selected from the group consisting of turmeric, *Curcuma xanthorrhiza* (*Zingiberaceae*), *Javan turmeric,* and *Curcuma zedoaria* (*Zingiberaceae*), to derive a curcuminoid extract; blending an effective amount of the boswellic-acid-containing extract and an effective amount of the curcuminoid-containing extract to form a dose; and orally administering the dose to the mammal. It is preferred that the dose be administered at least once each day for a period of at least seven days.

The method of the present invention also optionally include the steps of: extracting from a third botanical sample a gingerol-containing extract, the third botanical sample being at least one selected from the *Zingiber* genus and blending the gingerol-containing extract with the dose; extracting from a fourth botanical sample a capsaicinoid-containing extract, the fourth botanical sample being at least one selected from the *Capsicum* genus and blending the capsaicinoid-containing extract with the dose; extracting from a fifth botanical sample a bioflavonoid-containing extract and blending the bioflavonoid-containing extract (for example, derived from quercetin) with the dose; and blending a vitamin C source with the dose.

Other preferred compositions of the present invention for treating inflamation of connective tissue in humans comprise: boswellic acid, a curcuminoid, a gingerol, a capsaicinoid, a bioflavonoid, and vitamin C source, all preferably extracted from a botanical source.

Still another preferred embodiment of the invention is a composition comprising, in parts by weight, about 10 to 1800 parts of *Boswellia* gum extract comprising at least about 10% by weight of boswellic acids, more preferably at least about 30% by weight of boswellic acids, and most preferably at least about 50% by weight of boswellic acids, and about 50 to 400 parts of turmeric gum extract comprising at least about 30% by weight of curcuminoids, more preferably at least about 50% by weight of curcuminoids, and most preferably at least about 70% by weight of curcuminoids. Preferably, the composition further comprises about 40 to 1000 parts of ginger rhizome extract comprising at least about 1% by weight of gingerols, more preferably at least about 2% by weight of gingerols, and most preferably at least about 2.5% by weight of gingerols. Further, the composition preferably additionally comprises about 20 to 500 parts of bioflavonoids. These bioflavonoids are preferably selected from the group consisting of quercetin, isoquercetin, hesperidin, rutin, troxirutin, naringen, naringenin, limonene, chrysin, isoflavones, proanthocyanidins, anthocyanidins, ellagic acid, catechin, tannin, and mixtures thereof. Citrus bioflavonoids are especially preferred bioflavonoids. In still another embodiment of the invention the composition preferably further comprises about 20 to 500 parts of cayenne pepper and/or about 100 to 500 parts of vitamin C. In yet another embodiment of the invention, the composition preferably further comprises about 20 to 500 parts of a mineral selected from the group consisting of calcium, phosphorus, and mixtures thereof. A still further preferred embodiment of the invention is in the form of a tablet and further comprises an effective amount of an additive selected from the group consisting of diluents, binders, lubricants, disintegrators, colors, flavoring agents, and mixtures thereof. Preferred additives can be selected from the group consisting of dicalcium phosphate, microcrystalline cellulose, stearic acid, gum acacia, silica, magnesium stearate, and mixtures thereof.

DETAILED DESCRIPTION OF THE PREFERRED EMBODIMENTS OF THE PRESENT INVENTION

As is well known, many mammals suffer pain and disability from inflamation of connective tissues, particularly the tissue which makes up joints. Rheumatic diseases, such as those that primarily involve joints and which are generally known as arthritis, and those involving other connective tissues which are generally known as connective tissue diseases, impair or cripple millions. Such diseases cause huge personal and financial drains all around the world. The present invention provides a safe and effective mode of treatment of such diseases which provides benefits not heretofore available.

Importantly, in the description which follows various preferred compositions and methods of the present invention are disclosed but the scope of the present invention is not intended to be limited to the specific examples, process steps and materials disclosed herein. As will be understood, compositions, process steps and materials can vary significantly without diverging from the claimed invention.

In accordance with particular objects of the present invention, the primary ingredients of the presently preferred compositions described herein are derived from herbs such as *Boswellia*, turmeric, ginger, and *capsicum*. Each genus, family, or species, of herb provides benefits as will be fully described herein. Importantly, use of such herbal ingredients in accordance with the present invention provides relief from inflamation, pain, and swelling while avoiding the undesirable side effects of NSAIDs. Moreover, the compositions of the present invention provide herbal bioflavonoid and vitamin ingredients providing additional benefits including reducing pain and inflamation in mammalian connective tissue, particularly joints.

The compositions of the present invention preferably comprise extracts from plants belonging to at least one of following genera: *Boswellia, Commiphora,* and *Bursera* or closely related woody plant species of the family *Burseraceae,* from which an effective amount of one or more Boswellic acids are derived. The compositions of the present invention also preferably comprise extracts from plants providing a source of curcuminoids, such as from *Curcuma longa* (a common turmeric) rhizome, or from some other standardized turmeric ingredient which provides a concentrated curcuminoid extract.

While the present invention's use of botanical extracts provides many previously unrecognized benefits, it is necessary that the botanical extracts be properly prepared to realize the benefits of the present invention. In contrast to the techniques and procedures previously used by many in the industry when preparing compositions from botanical components, when formulating the compositions of the present invention, great care must be used to ensure that standardized dosage forms of each herb and standardized amounts of active ingredients are provided in the finished composition.

The term "standardized" as used herein is intended to refer to the process whereby the plant source and the appropriate plant parts, such as rhizome, bark, seed, and so forth, are accurately identified and processed so that amounts of active ingredients in the finished composition can be predicted and thus the physiological effect of the active ingredients also anticipated. For example, a qualified botanist can utilize biochemical markers to confirm true plant identification.

Furthermore, during standardized processing of the herbs in accordance with the present invention, the extraction process which is employed to concentrate bioactive compounds found in the plants must be carefully carried out to realize many of the benefits of the present invention. Moreover, also in accordance with the present invention, analytical techniques are preferably used to ensure that the desired active compounds are present in the botanical components, at the desired levels, in the specific herbal concentrates used to make up the finished composition.

As used herein, the term "effective amount" means an amount necessary to achieve a selected result. For example, administration of an effective amount of a boswellic acid or a curcuminoid will result in the desired reduction in pain and/or inflamation. By way of further example, an effective amount of a disintegrant is an amount such that a tablet formulation of the composition disintegrates to a selected extent within a selected period of time. Such an effective amount can be readily determined without undue experimentation by a person of ordinary skill in the art.

In accordance with the present invention, the botanical extracts used in the preferred compositions of the present invention can assume many forms but preferably include one or more exudate gums or standardized gum extracts derived from an appropriate botanical source. For example, a preferred source of Boswellic acids are the trees of the genus *Boswellia,* the genus *Commiphora,* the genus *Bursera,* or closely related woody plant species of the family *Burseraceae.* Also included in the preferred compositions of the present invention are curcuminoids. One preferred botanical source for the curcuminoids is common turmeric rhizome (*Curcuma longa*). Other preferred sources of curcuminoids preferably include a concentrated source of curcuminoids, such as extracted from turmeric samples.

The trees of the genera *Boswellia, Commiphora, Bursera,* or closely related woody plant species of the family Burseraceae typically grow wild in the arid and semi-arid tropics and warm temperate zones of the world and contain high concentrations of boswellic acids and other closely related compounds. Boswellic acids influence mammalian, and particularly human, eicosanoid biosynthesis.

Eicosanoids, such as prostaglandins, are involved in the inflammation of connective tissue and the contraction/relaxation of muscles, chemotaxis (especially cells of the immune system), promotion/inhibition of platelet aggregation, inhibition of gastric acid secretion, and other physiological actions. Linoleic acid, an essential fatty acid, plays an important role in proper eicosanoid metabolism in humans.

Boswellic acid gum extracts have been reported to contain different sugars like D-galactose, D-arabinose, D-xylose and D-mannose as well as volatile oil and uronic acids. As used herein, the term "Boswellic acids" is intended to include related acids such as ββ-Boswellic acids, Acetyl-ββ-boswellic acid, keto -ββ-boswellic acid and any other related acid which is now known or which becomes known in the future which provides the therapeutic effect described herein.

Turmeric (also spelled tumeric and also sometimes referred to as Curcumin, *Curcuma longa*, Indian saffron, Saffron, Curcuminoids), a member of the ginger family, contains a variety of bioactive substances called curcuminoids. The most active component is curcumin, an orange-yellow volatile oil that includes three curcuminoids: turmerone, atlantone, and zingiberone. Curcuminoids are naturally occurring phytochemicals that have beneficial effects on human eicosanoid biosynthesis leading to a net decrease in the localized production of certain inflammatory eicosanoids at the site of disease or trauma. Although curcuminoids are found in high concentrations in turmeric root, they are also present in other related plant species, such as *Curcuma xanthorrhiza* (*Zingiberaceae*) or *Javan turmeric,* and *Curcuma zedoaria* (*Zingiberaceae*), also known to practitioners of Chinese medicine as Shoti or Zedoary, which can readily substitute for common Indian turmeric.

In addition to boswellic acids and curcuminoids, the compositions of the present invention optionally include, in a herbaceous blend, ginger (preferably *Zingiber officinalis*), a rich source of gingerols. Ginger contains many active ingredients, including phenylalkylketones (gingerols, shogaols, and zingerone) and volatile oils (zingiberone, bisabolene, camphene, geraniol, linalool, and borneol). Ginger provides benefits when treating indigestion and flatulence, and it has a broad range of action against intestinal parasites. Gingerols and other active ingredients in ginger provide beneficial anti-inflammatory properties and reductions in blood platelet clumping. Gingerols are compounds that also inhibit 5-lipoxygenase in humans, and therefore reduce biosynthesis of certain inflammatory thromboxanes. See Kiuchi F., Iwakami S., Shibuya M., Hanaoka F., Sankawa U., Inhibition of prostaglandin and leukotriene biosynthesis by gingerols and diarylheptanoids, Chem. Pharm. Bull. (Tokyo) 1992 February;40(2):387–391. The ginger is preferably provided in the form of ginger rhizome extract.

The compositions of the present invention also optionally include cayenne pepper (*Capsicum annuum*). Cayenne pepper is a source of capsaicinoids. Capsaicinoids are vanilyl fatty acid amides that provide the characteristic "hot" and spicy pungency to foods containing certain peppers and capsaicin acts specifically at the site of inflammation by depleting stores of substance P from sensory neurons therefore blocking the transmission of painful stimuli to the brain. See Garrett N. E., Cruwys S. C., Kidd B. L., Tomlinson D. R., Effect of capsaicin on substance P and nerve growth factor in adjuvant arthritic rats, Neurosci Lett Jul, 11, 1997; 230 (1):58.

It is believed that the mechanism responsible for the beneficial effects of some of the ingredients described herein is the reduction of pain and inflammation by interference with the development of an exaggerated inflammatory response mediated by the activity of several enzymes catalyzing the synthesis of prostaglandins and leukotrienes and the inhibition of platelet aggregation.

It is also believed that inhibition of 5-lipoxygenase and C3-convertase is thought to play the key role in the reduction in pain and inflammation observed with use of certain plant medicines containing boswellic acids, curcuminoids, capsicum and gingerols. See Ammon H. P., Safayhi H., Mack T., Sabieraj J., "Mechanism of antiinflammatory actions of curcumine and boswellic acids," J. Ethnopharmacol March 1993;38 (2–3):113–11 9, Department of Pharmacology, Eberhard-Karls University, Tubingen, FRG; Safayhi H., Mack T., Sabieraj J., Anazodo M. I., Subramanian L. R., Ammon H. P., "Boswellic acids: novel, specific, nonredox inhibitors of 5-lipoxygenase," J Pharmacol Exp Ther 1992 June;261(3):1143–11 46, Department of Pharmacology, University of Tuebingen, FRG.

On the other hand, in accordance with the present invention, *Boswellia serrata* extracts appear to have little or no influence on cycleoxygenase activity and are used in accordance with the present invention as alternative anti-inflammatory agents for use where NSAIDs may otherwise be contraindicated in a patient for the treatment of numerous ailments, e.g., symptomatic treatment of rheumatoid arthritis, osteoarthritis, juvenile rheumatoid arthritis, soft tissue rheumatism, gout, low back pain, myositis and fibrositis.

Some of the most significant beneficial effects of *Boswellia serrata* on inflammation may include reduction of joint swelling, restoration and improvement of blood supply to inflamed joints, pain relief, increased mobility, reduced morning stiffness, steroid sparing, reduced disability and general improvement in quality of life and in performance of the routine activities of daily living. See Kulkami R. R., Patki P. S., Jog V. P., Gandage S. G., Patwardhan B., "Treatment of osteoarthritis with a herbomineral formulation: a double-blind, placebo-controlled, cross-over study," J Ethnopharmacol 1991 May;33(1–2):91–95.

Curcumin, a phytochemical component of turmeric, is known to inhibit human platelet aggregation induced by arachidonic acid, adrenaline and collagen. In vitro, it inhibits thromboxane $B_2$ production from arachidonic acid and increases formation of 12-lipoxygenase products. *Curcumin* also inhibits incorporation of carbon into platelet phospholipids and inhibits the deacylation of phospholipids on stimulation with calcium. Curcumin's anti-inflammatory properties in vivo are believed to be related to its effects on eicosanoid biosynthesis in humans.

Ginger provides additional antiinflammatory benefits. The anti-inflammatory effects of ginger are reportedly attributable to the presence of gingerols. It is also reported that the active components of ginger inhibit cyclooxygenase and 5-lipoxygenase activity in a manner that inhibits biosynthesis of prostaglandin E2 (PGE-2) and leukotriene B4 (LTB4), respectively. See Srivastava K. C., Mustafa T., Med Hypotheses 1992, "Ginger (*Zingiber officinale*) in rheumatism and musculoskeletal disorders," December; 39 (4):342–348, Department of Environmental Medicine, Odense University, Denmark. The inhibitory effects of the active components of ginger on cyclo-oxygenase activity, a key enzyme system required for biosynthesis of prostaglandins, which are active in the etiology of acute and chronic inflammation as well as cytoprotection of the gastric mucosa, is expected to be confirmed in the future. Anti-platelet activity and inhibition of thromboxane synthetase (5-lipoxygenase) are the most likely mechanisms proposed to explain the observed biological activity of ginger as an antiinflammatory agent. See Guh J. H., Ko F. N., Jong T. T., Teng C. M., "Antiplatelet effect of gingerol isolated from *Zingiber* officinale," J Pharm Pharmacol 1995 April;47(4):329–332; Kiuchi F., Iwakami S., Shibuya M., Hanaoka F., Sankawa U., "Inhibition of prostaglandin and leukotriene biosynthesis by gingerols and diarylheptanoids," Chem Pharm Bull (Tokyo) 1992 February;40(2):387–391.

A potential advantage of *Boswellia serrata*, ginger and turmeric, alone or in combination, as well as the other botanical extracts described herein, is low gastrotoxicity compared to now available NSAIDs and other drug therapies. NSAIDs are contraindicated among patients who have a history of gastric ulcers or other chronic gastric conditions. NSAID use also increases the risk of developing new gastric ulcers among those who have had no history of ulcer disease. The present invention thus provides the great advantage of providing an alternative agent which can be used for relief of pain and inflammation which does not increase the risk of developing new gastric ulcers or exacerbate existing conditions in patients requiring medication for chronic pain.

It is recognized in the art that development of selective NSAIDs, which inhibit 5-lipoxygenase without also inhibiting cyclo-oxygenase, would be a great advance. Thus, the embodiments of the present invention, which provide a natural, botanical-based composition with appropriate anti-inflammatory properties, fulfill a long felt need in the industry. Moreover, the embodiments of the present invention provide the unexpected safety benefits of a selective, natural 5-lipoxygenase inhibiting composition providing further advantages when treating arthritis and other inflammatory conditions.

Another optional component included in the compositions of the present invention is quercetin. Quercetin is a bioflavonoid and a natural reverse transcriptase blocker commonly found in red apples and red onions. Quercetin has been shown to have antiviral activity against HIV, herpes simplex, and the respiratory syncytial virus. Kaul, T. N., Middleton E., & Ogra P. L. "Antiviral effects of flavonoids on human viruses," J Med Virol, 15: 71–79, 1985 and Vrijsen, R., Everaert, L., & Boeye A. "Antiviral activity of flavones and potentiation by ascorbate," J Gen Virol 69: 1749–51, 1988.

Flavonoids (also called bioflavonoids) are natural botanical pigments that provide protection from free-radical damage, among other functions. Bioflavonoids provide protection from damaging free radicals and are believed to reduce the risk of cancer and heart disease, decrease allergy and arthritis symptoms, promote vitamin C activity, improve the strength of blood vessels, block the progression of cataracts and macular degeneration, treat menopausal hot flashes, and other ailments. Flavonoids occur in most fruits and vegetables. It is believed that flavonoids act by inhibiting hormones, such as estrogen, that may trigger hormone-dependent malignancies like cancers of the breast, endometrium, ovary, and prostate.

Limonene, a flavonoid available in citrus fruits, promotes the production of enzymes that help destroy possible carcinogens (cancer-causing agents). In addition, studies show that quercetin—another flavonoid found in citrus fruits—can block the spread of cancer cells in the stomach. Flavonoids also stabilize mast cells, a type of immune cell that releases inflammatory compounds, like histamine, when facing foreign microorganisms. Histamine and other inflammatory substances are involved in allergic reactions. Mast cells are large cells present in connective tissue. Flavonoids fortify and repair connective tissue by promoting the synthesis of collagen. Collagen is a remarkably strong protein of the connective tissue that "glues" the cells together. Flavonoids are believed to benefit connective tissue and reduce inflammation.

Citrus bioflavonoids include isoquercetin, quercetin, hesperidin, rutin, naringen, naringenin, and limonene. Isoquercetin is a common flavonoid found in onions, apples, *Arnica* species, *Gossypium arboreum*, *Ginko biloba*, *Ricinus communis*, *Ocimum basilicum*, *Salix acutifolia*, and *Narcissus pseudonarcissus*. Rich dietary sources of quercetin are onions, apples, kale, sweet cherries, grapes, red cabbage, and green beans. Hesperidin is found in the rinds of oranges and lemons. It helps strengthen capillary walls in conjunction with vitamin C. Naringen is found in grapefruit and is responsible for most of grapefruit's bitter taste. Other bioflavonoids include: isoflavones, proanthocyanidins, anthocyanidins, ellagic acid, catechin, and tannin.

Isoquercetin shares the same aglycone with rutin and quercitrin: quercetin. It has been shown that quercetin-containing glycosides liberate quercetin in the intestinal tract. Therefore, it is justified to assume that all the pharmacological properties of quercetin are also shared by isoquercetin and rutin when administered orally. Recent investigation demonstrated a rapid absorption of isoquercetin and quercetin-glucosides by the sodium-dependent glucose transport pathway in the small intestine. Due to superior bioavailability, the health effects of isoquercetin are increased compared to other flavonoids. Isoquercetin is known to have anti-inflammatory activity without adverse effects on the gastrointestinal tract, such as those caused by NSAIDs. Isoquercetin further exhibits beneficial effects as an antioxidant, antihypertensive, anticarcinogenic, antimicrobial, and analgesic agent.

Other bioflavonoids that can be added advantageously to the compositions of the present invention include troxirutin, and chrysin, which contains analgesic properties related to benzodiazepine receptor agonism.

The benefits of vitamin C are well known. In accordance with the present invention, a vitamin C source can preferably include those vitamin C sources known in the industry and particularly those selected from the group consisting of ascorbic acid, ascorbyl palmitate, and mineral ascorbates.

Isoflavones which are found in soy foods such as soybeans, tofu, tempeh, soy milk, textured vegetable protein, soy flour, and miso. Two significant isoflavones are genistein and daidzein.

Proanthocyanidins that are bound together are collectively called proanthocyanidin oligomers, or PCOs. PCOs are plentiful in grape seeds, red wine, and extracts of the bark of the maritime pine.

Anthocyanidins are plant pigments responsible for the red- to blue-red colors in blackberries, raspberries, blueberries, and cherries. When consumed, anthocyanidins attach to connective tissue, where they strengthen collagen.

Ellagic acid, a flavonoid in fruits (especially grapes) and vegetables, appears to directly protect genes from toxic compounds.

It is also within the scope of the present invention to add certain minerals to the compositions described herein. Many people, particularly those people living in North America, do not currently consume enough calcium. Calcium is important in the maintenance of bones and teeth, where it is primarily found with phosphorus as hydroxyapatite. Calcium also plays extremely important roles in cell communication and the regulation of body processes. Calcium also helps regulate enzymes and is necessary in blood clotting. It is involved in transmitting chemical and electrical signals along nerves and muscles, and is necessary for the release of neurotransmitters, which allow nerve impulses to pass from one nerve to another and from nerves to tissues. Calcium also plays a role in blood pressure regulation, possibly by controlling the contraction of muscles in the blood vessel walls and signaling the secretion of substances that regulate blood pressure. Inside muscle cells, calcium allows two muscle proteins, actin and myosin, to interact to cause muscle contraction. It is not possible to precisely estimate the dietary intake needed for maximum retention of calcium, thus, rather than a recommended dietary allowance (RDA), an adequate intake (AI) for adults age 19 through 50 years of 1000 mg per day has been determined. Since calcium absorption decreases with age, the AI for older adults is 1200 mg per day. For adolescents the AI is higher than for adults-1300 mg per day for boys and girls age 9 through 18.

Phosphorus makes up about 1% of the adult body by weight, and 85% or this is found as a structural component of bones. Phosphorus is also a component of phospholipids, which form the structure of cell membranes. Phosphorus is also a major constituent of DNA and RNA. Phosphorus is also involved in regulating enzyme activity because addition of a phosphate group can activate or deactivate certain enzymes. The high-energy bonds of ATP are formed between phosphate groups. Phosphorus as phosphate is an important buffer that helps regulate the pH in the cytoplasm of all cells. For adults 19 to 50 years of age, the RDA for phosphorus is 700 mg.

As described previously, the compositions of the present invention may be manufactured in tablet, liquid, or powder form. In powder form, the various dry, powdered ingredients are mixed together until a relatively homogeneous mixture is obtained. The powder is generally administered by mixing with a liquid, such as water or fruit juice, and then drinking the resulting suspension. In liquid form, the powder is mixed with an appropriate liquid carrier, preferably water, and the resulting suspension is packaged in appropriate containers. In tablet form, the ingredients are mixed together and then the tablets prepared according to methods well known in the art: (1) the wet-granulation method, (2) the dry-granulation method, or (3) direct compression. See Remington's Pharmaceutical Sciences.

As used herein, "tablets" are solid dosage forms containing the active substances with or without suitable additives and prepared either by compression or molding methods well known in the art. See Remington's Pharmaceutical Sciences. Tablets are a preferred dosage form because of the advantages afforded both to the manufacturer (e.g., simplicity and economy of preparation, stability, and convenience in packaging, shipping, and dispensing) and the user (e.g., accuracy of dosage, compactness, portability, blandness of taste, and ease of administration). Although tablets are most frequently discoid in shape, they may also be round, oval, oblong, cylindrical, or triangular. They may differ greatly in size and weight depending on the amounts of active substances present and the intended method of administration. They are divided into two general classes, (1) compressed tablets, and (2) molded tablets or tablet triturates. In addition to the active ingredients, tablets contain a number or inert materials or additives. A first group of such additives includes those materials that help to impart satisfactory compression characteristics to the formulation, including diluents, binders, and lubricants. A second group of such additives helps to give additional desirable physical characteristics to the finished tablet, such as disintegrators, colors, and flavoring agents.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, and the like.

As used herein, "binders" are agents used to impart cohesive qualities to the powdered material. Binders, or "granulators" as they are sometimes known, impart a cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as gum acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like.

As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils. Preferred amounts of lubricants range from about 0.1% by weight to about 5% by weight.

As used herein, "disintegrators" or "disintegrants" are substances that facilitate the breakup or disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, "coloring agents" are agents that give tablets a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye.

As used herein, "flavoring agents" are compounds designed to give the tablet a more palatable taste. Flavoring agents vary considerably in their chemical structure, ranging from simple esters, alcohols, and aldehydes to carbohydrates and complex volatile oils. Synthetic flavors of almost any desired type are now available and are well known in the art.

The following examples provide illustrative representations of the effectiveness of some preferred compositions within the scope of the present invention. The following examples are not intended to limit the scope of the claims set forth herein.

EXAMPLE 1

One preferred composition includes an effective daily dose of boswellic acids from *B. serrata* which is generally found to be from about 10 to about 1800 mg/day, and more preferably from about 400 to about 800 mg/day, administered as one dose, or more preferably two or three doses, consumed orally to a human with the addition of *Curcuma longa* (turmeric) and *Zingiber officinalis* (ginger) extracts being included with the *Boswellia serrata* extract at a dose of between about 10 and about 500 mg/day, and more preferably between about 100 and about 300 mg/day of curcuminoids and about 2 to about 50 mg/day, and more preferably about 5 to about 20 mg/day, gingerols also divided into two or three doses. While it is preferred that the doses be shaped in tablet form, it is also within the scope of the present invention to administer the dose in powder or liquid forms. Desirable results may be first noticed within hours after administration of the preferred compositions of the present invention with the inflamation symptoms subsiding substantially within days or a week after administration with continued improvement in the inflamation symptoms being further observed after three to four weeks following the beginning of treatment.

EXAMPLE 2

Another preferred composition of the present invention includes boswellic acids extracted from *B. serrata* in an amount from about 400 to about 800 mg/day, an extract of *Curcuma longa* (turmeric) providing between about 100 and about 300 mg/day of curcuminoids and an extract of *Zingiber officinalis* (ginger) providing between about 5 and about 20 mg/day gingerols, all divided into two or three doses administered orally to a human with the addition of capsaicin (from cayenne pepper) which provides additional benefits by partly depleting substance P and blocking transmission of pain stimuli. Additionally, lemon bioflavonoids and ascorbic acid have been included in this example in effective amounts for additional anti-inflammatory effect. A reduction in inflamation symptoms in a human is observed within hours after beginning treatment with the composition of this example and continued improvement is obtained within three to four weeks after beginning treatment.

EXAMPLE 3

Another preferred exemplary composition of the present invention includes extracts from *Boswellia serraffa* (*Shallaki* in Sanskrit), turmeric (*Curcuma longa* or *Haridra* in Sanskrit), and ginger (*Zingiber officinalis*). The exemplary composition of this example is orally administered to a human every day and provides relief from pain and inflammation. Using the composition of this example, a reduction in inflamation symptoms in a human is obtained shortly after beginning treatment.

EXAMPLE 4

Another preferred example of the present invention includes the following components:

| Component | Percent by weight | Ingredient constraints |
| --- | --- | --- |
| Boswellia serrata extract | 27.6 | not less than 70% boswellic acids by weight |
| Turmeric rhizome extract | 20.7 | not less than 95% Curcuminoids by weight |
| Ginger rhizome (*Zingiber officinalis*) extract | 13.8 | not less than 5% gingerols by weight |
| Cayenne pepper (*Capsicum annuum*) | 3.5 | powdered fruit |
| Lemon bioflavonoids | 13.8 | not less than 50% flavonols by weight |
| Quercetin | 7 | |
| Vitamin C (ascorbic acid) | 13.6 | |
| TOTAL | 100.0 | |

Administration of the composition of this example to a human provides excellent reduction in inflammation symptoms.

Administration of the composition of this example to a human provides excellent reduction in inflammation symptoms.

EXAMPLE 5

A further preferred example of the present invention includes the following components:

| Component | Percent by weight | Ingredient constraints |
|---|---|---|
| *Boswellia serrata* extract | 20 | not less than 70% boswellic acids by weight |
| Ginger rhizome (*Zingiber officinalis*) extract | 20 | not less than 5% gingerols by weight |
| Cayenne pepper (*Capsicum annuum*) | 5 | powdered fruit |
| Lemon bioflavonoids | 10 | not less than 50% flavonols by weight |
| Quercetin | 10 | |
| Vitamin C (ascorbic acid) | 10 | |
| TOTAL | 100.0 | |

Administration of the composition of this example to a human provides excellent reduction in inflamation symptoms.

Administration of the composition of this example to a human provides excellent reduction in inflamation symptoms.

EXAMPLE 6

Another preferred example of the present invention includes the following components:

| Component | Percent by weight | Ingredient constraints |
|---|---|---|
| *Boswellia serrata* extract | 50 | not less than 70% boswellic acids by weight |
| *Turmeric rhizome* (*Curcuma longa*) extract | 10 | not less than 95% curcuminoids by weight |
| Ginger rhizome (*Zingiber officinalis*) extract | 10 | not less than 5% gingerols by weight |
| Cayenne pepper (*Capsicum annuum*) | 5 | powdered fruit |
| Lemon bioflavonoids | 10 | not less than 50% flavonols by weight |
| Quercetin | 5 | |
| Vitamin C (ascorbic acid) | 10 | |
| TOTAL | 100.0 | |

Administration of the composition of this example to a human provides excellent reduction in inflamation symptoms.

Administration of the composition of this example to a human provides excellent reduction in inflamation symptoms.

EXAMPLE 7

Still another preferred example of the present invention includes the following components:

| Component | Percent by weight | Ingredient constraints |
|---|---|---|
| *Boswellia serrata* extract | 50 | not less than 70% boswellic acids by weight |
| *Turmeric rhizome* (*Curcuma lonaa*) extract | 10 | not less than 95% curcuminoids by weight |
| Ginger rhizome (*Zingiber officinalis*) extract | 10 | not less than 5% gingerols by weight |
| Cayenne pepper *Caosicum annuum* | 5 | powdered fruit |
| Lemon bioflavonoids | 10 | not less than 50% flavonols by weight |
| Quercetin | 5 | |
| Vitamin C (ascorbic acid) | 10 | |
| TOTAL | 100.0 | |

Administration of the composition of this example to a human provides excellent reduction in inflamation symptoms.

Administration of the composition of this example to a human provides excellent reduction in inflamation symptoms.

EXAMPLE 8

Yet another preferred example of the present invention includes the following components:

| Component | Percent by weight | Ingredient constraints |
|---|---|---|
| *Boswellia carterii* (common Frankincense), gum | 50 | not less than 70% boswellic acids by weight |
| *Turmeric rhizome Curcuma lonaa*) extract | 10 | not less than 95% curcuminoids by weight |
| Ginger rhizome (*Zingiber officinalis*) extract | 10 | not less than 5% gingerols by weight |
| Cayenne pepper *Capsicum annuum* | 5 | powdered fruit |
| Lemon bioflavonoids | 10 | not less than 50% flavonols by weight |
| Quercetin | 5 | |
| Vitamin C (ascorbic acid) | 10 | |
| TOTAL | 100.0 | |

Administration of the composition of this example to a human provides good reduction in inflamation symptoms.

Administration of the composition of this example to a human provides good reduction in inflamation symptoms.

EXAMPLE 9

A further preferred example of the present invention includes the following components:

| Component | Percent by weight | Ingredient constraints |
|---|---|---|
| *Boswellia serrata* (Indian Frankincense), gum | 50 | boswellic acids not less than 70% by weight |
| Turmeric rhizome (*Curcuma lonaa*) extract | 10 | not less than 95% curcuminoids by weight |
| Ginger rhizome (*Zingiber officinalis*) extract | 10 | not less than 5% gingerols by weight |
| Cayenne pepper | 5 | powdered fruit |
| Lemon bioflavonoids | 5 | not less than 50% flavonols by weight |
| Quercetin | 5 | |
| Vitamin C (ascorbic acid) | 10 | |
| Gamma linolenic acid | 5 | |
| TOTAL | 100.0 | |

Administration of the composition of this example to a human provides good reduction in inflamation symptoms.

Administration of the composition of this example to a human provides good reduction in inflamation symptoms.

In addition to the examples described above, a number of exemplary formulations of the present invention are provided below. Each of these additional formulations provides effective treatment for humans and other mammals in reducing pain and/or inflammation of connective tissue with consistent oral administration. Importantly, all of these exemplary formulations provide relief from pain and inflammation without causing the gastric disturbance which is common with treatment with NSAIDs. Understanding that these formulations are merely exemplary and not limiting of the present invention, the dietary supplement formulations will be set forth in percent by weight in Tables A and B.

TABLE A (in percent by weight)

| Botanical Component/ Formulation No. | I | II | III | IV | V |
|---|---|---|---|---|---|
| Boswellic acids | 20–70 | 20–70 | 20–70 | 20–70 | 20–70 |
| curcuminoids | 5–40 | 5–40 | 5–40 | 5–40 | 5–40 |
| gingerols | | 5–30 | 5–30 | 5–30 | 5–30 |
| capsaicin | | | 1–10 | 1–10 | 1–10 |
| bioflavonoids | | | | 1–20 | 1–20 |
| Vitamin C | | | | | 5–25 |

TABLE B (in percent by weight)

| Botanical Component/ Formulation No. | VI | VII | VIII | IX | X | XI | XII | XIII | XIV | XV | XVI | XVII | XVI | XVI | XVIII |
|---|---|---|---|---|---|---|---|---|---|---|---|---|---|---|---|
| *Boswellia serrata* (Indian Frankincense) extract | 20–70 | 20–70 | 20–70 | 20–70 | 20–70 | 20–70 | 20–70 | 20–70 | 20–70 | 20–70 | 20–70 | 20–70 | 20–70 | 20–70 | 20–70 |
| Turmeric rhizome (*Curcuma longa*) extract | 10–40 | 10–40 | 10–40 | 10–40 | 10–40 | 10–40 | 10–40 | 10–40 | 10–40 | 10–40 | 10–40 | 10–40 | 10–40 | 10–40 | 10–40 |
| Ginger rhizome (*Zingiber officinalis*) extract | | 5–30 | 5–30 | 5–30 | 5–30 | 5–30 | 5–30 | 5–30 | 5–30 | 5–30 | 5–30 | 5–30 | 5–30 | | |
| Cayenne pepper (*Capsicum annuum*) | | | 1–10 | 1–10 | 1–10 | 1–10 | 1–10 | 1–10 | 1–10 | 1–10 | 1–10 | 1–10 | 1–10 | | |
| Lemon bioflavonoids | | | 2–20 | 2–20 | 2–20 | 2–20 | 2–20 | 2–20 | 2–20 | 2–20 | 2–20 | | 2–20 | 2–20 | 2–20 |
| Quercetin | | | 1–10 | 1–10 | 1–10 | 1–10 | 1–10 | 1–10 | 1–10 | 1–10 | 1–10 | | 1–10 | 1–10 | 1–10 |
| Vitamin C (ascorbic acid) | | | | 5–25 | 5–25 | 5–25 | 5–25 | 5–25 | 5–25 | 5–25 | 5–25 | | 5–25 | 5–25 | |
| *Callicarpa macrophylla* (Pringu) extract | | | | 0–10 | 0–10 | 0–10 | 0–10 | 0–10 | 0–10 | 0–10 | 0–10 | 0–10 | 0–10 | | 0–10 |
| *Crinum deflexum* (asiaticum) (Sudarshan) extract | | | | | 0–5 | 0–5 | 0–5 | 0–5 | 0–5 | 0–5 | 0–5 | 0–5 | 0–5 | | 0–5 |
| *Cyperus rotundus* (Mustaka) extract | | | | | | 0–5 | 0–5 | 0–5 | 0–5 | 0–5 | 0–5 | 0–5 | 0–5 | | 0–5 |
| *Psederia foetida* (Prasarini) extract | | | | | | | 0–5 | 0–5 | 0–5 | 0–5 | 0–5 | 0–5 | 0–5 | | 0–5 |
| *Boswellia bhau-dajiana* extract | | | | | | | | | | | 0–70 | 0–70 | 0–70 | 0–70 | 0–70 |
| *Boswellia frereana* extract-African | | | | | | | | | | | | 0–70 | 0–70 | 0–70 | 0–70 |
| *Boswellia papyrifera* extract - Sudanese | | | | | | | | | | | | 0–70 | 0–70 | 0–70 | 0–70 |
| *Boswellia sacra* extract-Saudi | | | | | | | | | | | | 0–70 | 0–70 | 0–70 | 0–70 |
| *Boswellia carterii* extract, (common Frankincense) gum | | | | | | | | | | | | 0–70 | 0–70 | 0–70 | 0–70 |
| *Commiphora incisa* extract | | | | | | | | | | | | 0–70 | 0–70 | 0–70 | 0–70 |
| *Commiphora myrrha* extract | | | | | | | | | | | | 0–70 | 0–70 | 0–70 | 0–70 |
| *Commiphora abyssinica* extract | | | | | | | | | | | | 0–70 | 0–70 | 0–70 | 0–70 |
| *Commiphora erthraea* extract | | | | | | | | | | | | 0–70 | 0–70 | 0–70 | 0–70 |

TABLE B-continued (in percent by weight)

| Botanical Component/ Formulation No. | VI | VII | VIII | IX | X | XI | XII | XIII | XIV | XV | XVI | XVII | XVI | XVI | XVIII |
|---|---|---|---|---|---|---|---|---|---|---|---|---|---|---|---|
| *Commiphora molmol* extract | | | | | | | | | | | 0–70 | 0–70 | 0–70 | | 0–70 |
| Gamma linolenic acid extract | | | | | | | | | | | 0–5 | 0–5 | 0–5 | | 0–5 |
| *Bursera microphylla\* extract - Elephant tree | | | | | | | | | | | 0–50 | 0–50 | 0–50 | | 0–50 |

EXAMPLE 10

A still further illustrative embodiment of the present invention comprises a dose of the following ingredients in tablet form: (1) *Boswellia* gum extract (standardized to 70% boswellic acids), 400 mg; (2) tumeric rhizome extract (standardized to 95% curcuminoids), 300 mg; (3) ginger rhizome extract (*Zingiber officinale*) (standardized to 5% gingerols), 200 mg; (4) cayenne pepper fruit (*Capsicum annuum*), 50 mg; (5) lemon bioflavonoid complex (standardized to 50% flavonols), 200 mg; (6) quercetin, 100 mg; (7) vitamin C, 200 mg, (8) calcium, 210 mg; (9) phosphorus, 161 mg; (10) and effective amounts of additives: dicalcium phosphate, microcrystalline cellulose, stearic acid, gum acacia, silica, and magnesium stearate.

In view of the forgoing, it will be appreciated that the present invention provides a composition which reduces acute and chronic inflammation in mammals and which can be conveniently orally administered. The present invention also provides a composition for use as a dietary supplement that is effective in treating the pain and discomfort of inflammatory ailments such as rheumatoid arthritis, osteoarthritis, juvenile rheumatoid arthritis, soft tissue rheumatism, gout, low back pain, minor soft tissue injuries, minor burns, sprains, headache, and general muscle soreness after exercise and exertion.

It will also be appreciated that the present invention provides a composition for use as a dietary supplement which improves the use of joints which are afflicted with arthritis and which reduces the swelling, pain and morning stiffness of arthritic joints and which increases range of motion, grip strength and general mobility in affected joints. The present invention also provides a dietary supplement composition which improves the general health, quality of life, and well being of those suffering from chronic inflammatory diseases, including rheumatism and arthritis.

It will be further appreciated that the present invention provides a safe and effective dietary supplement composition which can be used to reduce the dosage of, or replace, conventional Non-Steroidal Anti-Inflammatory Drugs for the symptomatic treatment of pain, inflammation and swelling in mammals and that the present invention provides a safe and effective composition for the treatment of pain, inflammation and swelling in individuals for whom NSAIDs are no longer desirable due to gastrotoxicity, gut intolerance or risk of renal damage.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of treating an ailment involving pain and inflammation in a mammal comprising administering to the mammal a composition comprising, in parts by weight, about 10 to 1800 parts of *Boswellia* gum extract comprising at least 10% by weight of boswellic acids, and about 50 to 400 parts of *turmeric* gum extract comprising at least about 30% by weight of curcuminoids.

2. The method of claim 1, wherein the composition further comprises gingerol.

3. The method of claim 1, wherein the composition further comprises bioflavonoids.

4. The method of claim 3, wherein the bioflavonoids are selected from the group consisting of quercetin, isoquercetin, hesperidin, rutin, troxirutin, naringen, naringenin, limonene, chrysin, isoflavones, proanthocyanidins, anthocyanidins, ellagic acid, catechin, and tannin.

5. The method of claim 3, wherein the bioflavonoids comprise citrus bioflavonoids.

6. The method of claim 1, wherein the composition further comprises cayenne pepper.

7. The method of claim 1, wherein the composition further comprises vitamin C.

8. The method of claim 1, wherein the composition further comprises a mineral selected from the group consisting of calcium and phosphorus.

9. The method of claim 1, wherein the ailment afflicts connective tissue.

10. The method of claim 1, wherein the ailment is selected from the group consisting of rheumatoid arthritis, osteoarthritis, juvenile rheumatoid arthritis, gout, low back pain, minor soft tissue injury, minor burn, sprain, headache, general muscle soreness, swelling, stiffness, and chronic inflammatory disease.

11. The method of claim 1, wherein the composition further comprises a non-steroidal anti-inflammatory drug.

\* \* \* \* \*